US008753858B2

(12) United States Patent
Qian et al.

(10) Patent No.: US 8,753,858 B2
(45) Date of Patent: Jun. 17, 2014

(54) REAGENTS AND PROCESSES FOR STABILIZING ALKALINE PHOSPHATASE OR CONJUGATES THEREOF

(75) Inventors: Chungen Qian, Shenzhen (CN); Yuping Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1 day.

(21) Appl. No.: 12/980,870

(22) Filed: Dec. 29, 2010

(65) Prior Publication Data
US 2011/0159565 A1    Jun. 30, 2011

(30) Foreign Application Priority Data

Dec. 31, 2009   (CN) .......................... 2009 1 0239511

(51) Int. Cl.
*C12N 9/16* (2006.01)
*C12N 9/96* (2006.01)
*C12N 9/98* (2006.01)

(52) U.S. Cl.
USPC .......................................... 435/188; 435/196

(58) Field of Classification Search
CPC ............... C12N 9/16; C12N 9/96; C12N 9/98
USPC ...................... 435/188, 195, 196; 252/182.29
See application file for complete search history.

(56) References Cited

U.S. PATENT DOCUMENTS

| | | | | | |
|---|---|---|---|---|---|
| 4,808,521 | A | * | 2/1989 | Allen ........................... | 435/7.93 |
| 5,093,231 | A | | 3/1992 | Hoke | |
| 5,998,156 | A | | 12/1999 | Sugiyama et al. | |
| 6,218,160 | B1 | | 4/2001 | Duan | |
| 6,669,963 | B1 | * | 12/2003 | Kampinga ..................... | 424/499 |
| 6,767,716 | B2 | * | 7/2004 | Giri ................... | 435/19 |
| 7,078,172 | B1 | | 7/2006 | Okamura et al. | |
| 2003/0190760 | A1 | * | 10/2003 | Watkins et al. ............... | 436/518 |
| 2004/0197885 | A1 | | 10/2004 | Ueda et al. | |
| 2006/0051809 | A1 | * | 3/2006 | Nazarenko et al. .............. | 435/6 |
| 2007/0141645 | A1 | | 6/2007 | Okamura et al. | |
| 2008/0254492 | A1 | | 10/2008 | Tsuchiya et al. | |
| 2009/0269825 | A1 | | 10/2009 | Kishimoto et al. | |
| 2011/0300601 | A1 | | 12/2011 | Qian et al. | |
| 2011/0300602 | A1 | | 12/2011 | Qian et al. | |

FOREIGN PATENT DOCUMENTS

| | | | |
|---|---|---|---|
| CN | 1120457 | A | 4/1996 |
| CN | 1381725 | | 11/2002 |
| CN | 1683407 | | 10/2005 |
| CN | 1986785 | A | 6/2007 |
| CN | 100353166 | C | 12/2007 |
| EP | 0709458 | A1 | 5/1996 |
| EP | 0794249 | A2 | 9/1997 |
| EP | 0702712 | B1 | 12/1998 |
| EP | 1978363 | | 2/2008 |
| GB | 1480089 | A * | 7/1977 |
| JP | 2003009857 | A | 1/2003 |
| WO | WO 2007055284 | A1 * | 5/2007 |

OTHER PUBLICATIONS

Haines "Non-equivalence of D and L-trehalose in stabilizing alkaline phosphatase against freeze-drying and thermal stress. Is chiral recognition involved?" Organic and Biomolecular Chemistry, 2006, vol. 4 702-706.*
Govardhan, Chandrika P.; "Crosslinking fo Enzymes for Improved Stability and Performance", Current Opinion Biotechnol, vol. 10, pp. 331-335, 1999.
Bieniarz, Christopher et al.; "Alkaline Phosphatase Activatable Polymeric Cross-Linkers and Their Use in the Stabilization of Proteins", Bioconjugate Chemistry, vol. 9, pp. 390-398, 1998.
Bieniarz, Christopher et al.; "Technical Notes: Thermally Stabilized Immunoconjugates: Conjugation of Antibodies to Alkaline Phosphatase Stabilized with Polymeric Cross-Linkers", Bioconjugate Chemistry, vol. 9, pp. 399-402, 1998.
Journal of Nanton Medical College 1996: 16(2); pp. 162-164, with English abstract.
Office Action dated Nov. 29, 2012 for U.S. Appl. No. 13/152,083.
Office Action dated Jul. 31, 2013 for U.S. Appl. No. 13/151,876.
Steidler et al., 'Functional Display of a Heterologous Protein on the Surface of *Lactococcus lactis* by Meand of the Cell Wall Anchor of *Staphylococcus aureus* Protein A', Applied and Environmental Microbiology, Jan. 1998, vol. 64, No. 1, pp. 342-345.
Lombardi et al., 'A Method for Selective Conjugation of an Analyte to Enzymes Without Unwanted Enzyme—Enzyme Cross-Linking', Analytical Biochemistry, 331, 2004, pp. 40-45.
Tan et al., 'Immobilization of Enzymes at High Load/Activity by Aqueous Electrodeposition of Enzyme-Tethered Chitosan for Highly Sensitive Amperometric Biosensing', Biosensors and Bioelectronics, 25, 2010, pp. 2644-2650.

* cited by examiner

*Primary Examiner* — Jon P Weber
*Assistant Examiner* — Charles Zoltan Constantine
(74) *Attorney, Agent, or Firm* — Kory D. Christensen; Matthew S. Bethards; Stoel Rives LLP

(57) ABSTRACT

The present disclosure relates to stabilizers for alkaline phosphatase or conjugates thereof, a process for preparing a stabilizer, and a method for stabilizing alkaline phosphatase or conjugates thereof with a stabilizer. The present disclosure also relates to a reagent of alkaline phosphatase or conjugates thereof as well as to a process for preparing the same. In another aspect, the present disclosure relates to a kit comprising the stabilizers disclosed herein and alkaline phosphatase or conjugates thereof. The stabilizer disclosed herein can stabilize alkaline phosphatase or conjugates thereof for a prolonged period of time, extending their shelf-life.

16 Claims, No Drawings

REAGENTS AND PROCESSES FOR STABILIZING ALKALINE PHOSPHATASE OR CONJUGATES THEREOF

RELATED APPLICATIONS

This application claims priority to Chinese Patent Application No. 200910239511.8, filed on Dec. 31, 2009, the disclosure of which is fully incorporated herein by reference.

TECHNICAL FIELD

The present disclosure relates to stabilizers for an enzyme. Specifically, the present disclosure relates to stabilizers for alkaline phosphatase or conjugates thereof, a process for stabilizing alkaline phosphatase or conjugates thereof with a stabilizer, and a reagent comprising a stabilizer and alkaline phosphatase or conjugates thereof.

DETAILED DESCRIPTION

Alkaline phosphatase (AP) is an enzyme widely found in various animals, plants and microorganisms. In general, commercial AP is extracted from calf intestinal mucosa and *Escherichia coli* and composed of a number of isoenzymes. In an appropriate buffer solution, AP catalyzes the hydrolysis of chromogenic substrates and chemiluminescent substrates which contain a phosphate group, such as p-nitrophenyl phosphate (PNP), sodium β-glycerophosphate, naphthyl phosphate, and 3-(2-spiroadamantane)-4-methoxy-4-(3-phosphoryloxy)-phenyl-1,2-dioxetane (AMPPD). Accordingly, AP may be widely used as a labeling enzyme in quantitative diagnostic clinical immunology.

A solution of AP or an AP conjugate may be one of the components included in a kit for in vitro diagnosis, and the stability of the enzymatic activity of AP may influence the performance of the kit. Like other biological enzymes, AP has a short half-life, and can be easily inactivated. It may be completely inactivated by a change of pH, salt ions, and temperature. As such, the long-term stability of AP or an AP conjugate in solution may be useful for a diagnostic kit.

Enzyme stability may be improved via chemical modification or the addition of additives.

Crystallization of a cross-linked enzyme (Curr Opin Biotechnol, 10:331-335, 1999) and the covalent conjugation of an enzyme polymer (Bioconjugate Chem, 9:390-398, 1998) are two technologies which may improve enzyme stability via chemical modification. Proteins and polymers were combined with AP (Bioconjugate Chem, 9:399-402, 1998), the enzyme activity of the AP was tested after incubation at 37° C. and 45° C., and an improvement in the activity of the modified AP was found. However, chemically modifying AP may be complex and difficult to control, thus this method may not be an option for diagnostic reagent products.

CN100353166C discloses an enzyme conjugate stabilizer for extending the shelf life of an enzyme conjugate solution in an immunoassay product containing the enzyme conjugate as a tracer. The stabilizer contains proteins, hemoglobin, anti-free radical substances, and a buffer solution.

CN1522298A discloses a process for stabilizing human derived AP, which incorporates an AP solution into albumin or dextran and a saccharide selected from the group consisting of galactose, lactose and fructose, and then freeze-drying the mixture.

CN1986785A discloses a composite enzyme stabilizer containing bovine serum albumin, EGTA, 1,2-dithiothreitol, potassium gluconate, sodium chloride, Proclin300, and magnesium acetate. The stabilizer stabilizes lactate dehydrogenase, sarcosine oxidase, urease, creatinine enzyme, creatine hydrolase, catalase, cholesterol oxidase, cholesterol esterase, and peroxidase.

Accordingly, a reagent which stabilizes AP or a conjugate thereof, may be useful.

In one aspect, the present disclosure relates to a stabilizer for alkaline phosphatase (AP) or conjugates thereof, comprising:

(1) a protein;
(2) an activator containing either magnesium or calcium ions, or both;
(3) zinc ions; and
(4) sodium ions.

In another aspect, a process for preparing a stabilizer for AP or conjugates thereof is disclosed, the process comprising dissolving each component of the stabilizer in water, and optionally drying the solution into a powder to obtain the stabilizer.

In another aspect, a method for stabilizing AP or conjugates thereof is disclosed, the process comprising dissolving the stabilizer and AP or conjugates thereof into a solution.

In another aspect, a reagent of AP or conjugates thereof is disclosed, the reagent comprising a stabilizer and AP or conjugates thereof.

In another aspect, a process for preparing a reagent of AP or conjugates thereof is disclosed, the process comprising blending a stabilizer and AP or conjugates thereof in water, and optionally drying the solution into a powder.

In another aspect, a kit is disclosed, the kit comprising a stabilizer and AP or conjugates thereof.

A stabilizer as disclosed herein, may stabilize AP or conjugates thereof for a prolonged period of time, and thus extend its shelf-life. In contrast to a conventional AP reagent, AP protected with a stabilizer as disclosed herein will retain its activity even after two weeks of exposure in an accelerated stability test at 37° C. The present disclosure may be useful for improving the stability and quality of immunoassay products containing AP or an AP conjugate, including enzyme protectant products, ELISA diagnostic kit products, and chemiluminescent immunoassay diagnostic kit products. Furthermore, it may be useful in a wide range of fields, such as clinical diagnosis, scientific research, environmental hygienic surveillance, and forensics.

Unless otherwise indicated, the term "soluble salt" as used herein is intended to mean any salt soluble in water, which includes but is not limited to halides, sulfates, carbonates, and phosphates.

A protein is generally included in commercial enzyme reagents as an enzyme protectant, and a common such protein is albumin. An action of albumin is adsorption, which may prevent AP from being denatured, and may prevent polymerization or aggregation resulting from the intermolecular attraction between AP molecules. Those skilled in the art will understand that other proteins may similarly be protective for AP, which may have an adsorption effect. For example, proteins such as casein, gelatin, and xanthan gum may be used as an enzyme protectant.

Alkaline phosphatase is a dimeric zinc containing metalloenzyme. Each monomeric enzyme subunit contains at least two zinc atoms. There are three kinds of metal binding sites, i.e., the so-called catalytic binding site (A), the structural binding site (B), and the regulatory binding site (C). The binding of zinc at two of the metal binding sites results in the phosphorylation of only one subunit. This may be termed a negative cooperative subunit interaction.

Although not wanting to be bound by theory, it is believed that the addition of metal ions such as $Mg^{2+}$ and $Ca^{2+}$ will bind at the B and C sites, and thus eliminate the above-mentioned negative cooperative subunit interaction. This results in the phosphorylation of both subunits of the dimer. In each subunit, $Zn^{2+}$ binds to three distinct histidine residues, at least one of which is located at site A.

Magnesium ions in the stabilizers of the present disclosure may originate from soluble salts containing magnesium ions, such as magnesium sulfate, magnesium acetate, magnesium chloride, and other salts from which magnesium ions can be dissociated in solution. Calcium ions in the stabilizers of the present disclosure may originate from soluble salts containing calcium ions, such as calcium acetate, calcium chloride, and any other salts from which calcium ions can be dissociated in solution.

Magnesium and calcium ions may be used in the stabilizers disclosed herein to activate AP, to improve the efficiency of the hydrolysis reaction it catalyzes. Furthermore, the magnesium and calcium ions in solution may come into contact with the protein, so as to improve the rigidity of the protein and increase its stability against factors such as temperature.

The concentration of magnesium or calcium ions in the solution may range from about 0.001 to about 0.01 mol/L. When a combination of magnesium and calcium ions is used, the sum of the concentration of magnesium and calcium ions may be within this range.

Zinc ions in the stabilizers of the present disclosure may originate from soluble salts containing zinc ions, such as zinc sulfate, zinc chloride, and other salts from which zinc ions can be dissociated in solution.

Alkaline phosphatase is a metalloenzyme containing zinc ions. As such, zinc ions are included in the stabilizers disclosed herein to prevent AP from losing zinc because of a chelating agent.

The appropriate concentration of the zinc ions dissociated from the solution of the soluble salt(s) containing zinc ion may range from about 0.01 to about 0.2 mmol/L.

Sodium ions may also be included in the stabilizers disclosed herein.

While not being bound by theory, it is believed that the sodium ions in the stabilizers of the present disclosure may bind to the zinc binding center of the AP, making the AP more stable as well as maintaining its enzymatic activity.

A high-salt environment is generally considered unfavorable for enzyme activity. Standard saline contains salt at a concentration of approximately 0.15 M. Surprisingly, we found that it is helpful for stabilizing AP if the sodium ions are used at a concentration as high as approximately 3.0 M.

In an embodiment, the concentration of sodium ions is between about 0.1 to about 3.0 mol/L. In another embodiment, the concentration of sodium ions is between about 0.15 to about 3.0 mol/L. In a further embodiment, the concentration of sodium ions is between about 0.2 to about 3.0 mol/L. Alternatively, the concentration of sodium ions may be at least about 0.2 mol/L, or at least about 0.5 mol/L.

Sodium ions in the stabilizer of the present disclosure may originate from soluble salts containing sodium ions, such as sodium chloride. The sodium chloride may be used at a concentration between about 8 g/L to about 175 g/L.

The deactivation or denaturation of proteins in solution may be caused by factors such as adsorption, protein aggregation, disulfide bond exchange by heat, hydrolysis by proteases, aspartate and glutamate deamination, racemization of amino acid residues, oxidation of cystine disulfide bonds, and oxidation of tryptophan indoles.

Optionally, the stabilizers disclosed herein may comprise an enzyme protectant to eliminate or reduce the above factors, which may be disadvantageous to AP activity.

Polyols which may be useful as the protectant include but are not limited to glycerol, mannitol, sorbitol, inositol, and xylitol. These polyols may be capable of forming a number of hydrogen bonds with proteins, which may contribute to the formation of a solvent layer and an increase in solvent surface tension. As a result, the AP may be solvated, and its stability may be improved.

The addition of glycerol in the stabilizers disclosed herein may aid the AP solution in forming a uniform suspension, which may help the AP suspended therein maintain its activity. Thus, the homeostasis of the AP equilibrium may then shift toward a stable form.

Polysaccharides which may be useful in the stabilizers disclosed herein as a protectant include but are not limited to galactose, lactose, fructose, sucrose, and trehalose. The presence of polysaccharides in an AP solution may inhibit denaturation. The polyol structure of these saccharides makes them capable of binding, through hydrogen bonding, to both the surface of the AP and external water molecules, which may contribute to the stabilization of the AP.

Surfactants which may be useful in the stabilizers disclosed herein as a protectant may be a nonionic surfactant. Useful nonionic surfactants include but are not limited to sorbitan polyoxyethylene ether fatty acid esters and alkylphenol polyoxyethylene ethers, such as sorbitan polyoxyethylene ether lauric acid ester type surfactants, sorbitan polyoxyethylene ether oleic acid ester type surfactants, and octylphenol polyoxyethylene ether type surfactants.

The protectant in the stabilizers of the present disclosure may further comprise polyethylene glycol (PEG). PEGs are capable of increasing the surface tension of the solvent. PEGs contain multiple oxygen atoms, which can surround the alkaline phosphatase to establish a stable micro environment and thus contribute to the stabilization of alkaline phosphatase molecules. PEGs also bind to the surface of AP, and thus stabilize it. In an embodiment, PEGs having a molecular weight over about 1000 may be included, due to their humectant properties. In a further embodiment, PEGs having a molecular weight of about 6000 to about 20000 may be included.

The protectants included in the stabilizers disclosed herein may be used either separately or as a combination of two or more. The protectant may be used in an range between about 0.1% to about 10% by weight.

Optionally, the stabilizer disclosed herein further comprises a preservative to facilitate the sterility and long-term preservation of the reagent. Commercially available preservatives such as Proclin300, sodium azide, Caisson, and gentamicin may be used with the stabilizers disclosed herein. The preservatives may be used at a concentration which does not affect the activity of the AP.

Optionally, the stabilizer disclosed herein further comprises a buffering agent to maintain the pH in a range of between about 7 to about 9. The buffering agent may be tris(hydroxymethyl)aminomethane (Tris), triethanolamine (TEA), diethanolamine (DEA), 2-methyl-2-amino-1-propanol (AMP), N-bis(2-hydroxyethyl)-2-Taurine (BHET), (Cyclohexylamino)-1-propanesulfonic acid (CAPSO), (Cyclohexylamino)-1-ethanesulfonic acid (CHES), 2-hydroxyethyl-piperazinyl-N-2-ethanesulfonic acid (HEPES), (N-Morpholinyl)ethanesulfonic acid (MES), 3-(N-morpholino)propanesulfonic acid (MOPS), piperazinyl-N,N-bis(2-ethanesulfonic acid) (PIPES), piperazinyl-N,N-bis(2-hydroxy ethanesulfonic acid) (POPSO), tris(hydroxymethyl)

methyl-3-amino propanesulfonic acid (TAPSO), Tris (hydroxymethyl)methyl-2-aminoethanesulfonic acid (TES), and N-2-hydroxyethyl-piperazinyl-N-3-propanesulfonic acid (HEPES). The pH value of the buffered solution may be between about 7.0 to about 8.0. The buffering agent may be used between about 10 to about 500 mM.

Optionally, the stabilizers disclosed herein further comprise a protease inhibitor which may prevent the AP from being hydrolyzed by protease. Inhibitors may include PMSF, Pepstatin, Leupeptin, and Aprotinin. The inhibitors may be used at their usual operating concentration.

The stabilizers disclosed herein may be preserved in a solution form or a dry powder form.

In another aspect, a process for preparing a stabilizer for AP or conjugates thereof is disclosed. The stabilizers disclosed herein may be prepared by dissolving the components into water. Alternatively, they may be prepared as a dry powder, for example, by lyophilization after the solution is obtained.

In another aspect, a method for stabilizing AP or conjugates thereof is disclosed, which comprises dissolving the stabilizers disclosed herein and AP into water to form a solution.

Specifically, a method for stabilizing AP or conjugates thereof may comprise dissolving a stabilizer as disclosed herein into water to form a solution and then incorporating the AP. Alternatively, a method may comprise dissolving a stabilizer as disclosed herein together with the AP in water to form a solution. A method may further comprise incorporating a stabilizer as disclosed herein into a pre-formulated solution of AP and forming a solution by mixing.

In another aspect, an AP reagent comprising the stabilizers disclosed herein and AP or conjugates thereof, is disclosed. A stabilizer as disclosed herein and the AP or conjugates thereof may be preserved in a solution form or in a dry powder form. The stabilizers disclosed herein and the AP or conjugates thereof may be preserved together, or they may be preserved separately and incorporated or dissolved together before use.

In another aspect, a process for preparing an AP reagent is disclosed, comprising dissolving a stabilizer as disclosed herein and AP or conjugates thereof into water to form a solution and optionally drying, for example by lyophilizing, the solution into a powder. Alternatively, the process may comprise mixing a stabilizer powder and the dry AP powder to prepare an AP reagent.

In another aspect, a kit comprising a stabilizer as disclosed herein and AP or conjugates thereof is disclosed, and optionally an appropriate substrate and/or coating solution.

To measure the activity of the stabilizers disclosed herein, an amount of AP or a conjugate thereof was added to a solution of a stabilizer as disclosed herein, and subjected to an accelerated stability test at 37° C. and a constant humidity. The stabilization effect of the stabilizer on the AP was evaluated by measuring the loss of enzymatic activity (100%-residual activity %) of the AP in the stabilizer. The loss of enzymatic activity of AP without a stabilizer was 7 to 70 times higher than that with a stabilizer, as shown by the following examples.

EXAMPLES

The present disclosure will be further described with references to the following examples. The examples are intended only to be illustrative, but not to limit the scope of the present disclosure in any sense. Unless otherwise indicated, all of the reagents used in the examples were supplied from Sigma-Aldrich Co.

The term "BSA" as used in the examples means "bovine serum albumin".

Example 1

An amount of AP was incorporated into the stabilizer solution formulated as below to form an enzyme solution at a final concentration of 5 µg/mL, and the solution was then subjected to an accelerated stability test in a thermostat at 37° C. and a constant humidity. Generally, the AP solution is placed at 37° C. for several weeks, and periodically a portion of the solution is removed for activity analysis. The higher temperature of the solution accelerates degradation reactions. The enzyme solution was then analyzed with a Mindray automatic biochemical analyzer BS300 and an accessory AP assay kit to determine the percent of residual AP activity in the solution (as a percentage of the activity after the accelerated stability test to that before the accelerated stability test).

The stabilizer solution was formulated as follows:

| BSA | 1% (g/100 ml) |
|---|---|
| $MgCl_2$ | 1 mM |
| Proclin 300 | 0.05% (g/100 ml) |
| Tris | 50 mM |
| pH was adjusted with HCl | to 7.5 |

As shown in the following Table 1, in the enzyme solution, the AP retained only 26% of its activity after one week of the accelerated stability test, and approximately 70% of its activity was lost. In this Example, no sodium or zinc ions were added.

TABLE 1

Residual AP activity

| | Days of the test | | | |
|---|---|---|---|---|
| | Day 1 | Day 2 | Day 7 | Day 8 |
| Residual activity percent | 75% | 65% | 33% | 26% |

Example 2

An amount of AP was incorporated into the stabilizer solution formulated as below to form an enzyme solution as described in Example 1.

The stabilizer solution was formulated as follows:

| BSA | 1% (g/100 ml) |
|---|---|
| $ZnCl_2$ | 0.1 mM |
| NaCl | 8 g/L |
| $MgCl_2$ | 1 mM |
| Proclin 300 | 0.05% (g/100 ml) |
| Tris | 50 mM |
| pH was adjusted with HCl | to 7.5 |

As shown in Table 2, in the enzyme solution, the AP lost 15% of its activity after two weeks of the accelerated stability test.

TABLE 2

| | Residual AP activity | | | |
| --- | --- | --- | --- | --- |
| | Days of the test | | | |
| | Day 8 | Day 9 | Day 11 | Day 14 |
| Residual activity percent | 86% | 86% | 83% | 85% |

Example 3

An amount of AP was incorporated into the stabilizer solution formulated as below to form an enzyme solution as described in Example 1

The stabilizer solution was formulated as follows:

| | |
| --- | --- |
| BSA | 1% (g/100 ml) |
| $ZnCl_2$ | 0.1 mM |
| NaCl | 100 g/L |
| Casein | 1% (g/100 ml) |
| Gelatin | 1% (g/100 ml) |
| $MgCl_2$ | 1 mM |
| Proclin 300 | 0.05% (g/100 ml) |
| Tris | 50 mM |
| pH was adjusted with HCl | to 7.5 |

As shown in Table 3, in the enzyme solution, the AP lost 10% of its activity after two weeks of the accelerated stability test. In this Example, the amount of NaCl added was larger than that of Example 2, and casein and gelatin were added.

TABLE 3

| | Residual AP activity | | | |
| --- | --- | --- | --- | --- |
| | Days of the test | | | |
| | Day 3 | Day 8 | Day 14 | Day 16 |
| Residual activity percent | 95% | 91% | 90% | 94% |

Example 4

An amount of AP was incorporated into the stabilizer solution formulated as below to form an enzyme solution as described in Example 1.

The stabilizer solution was formulated as follows:

| | |
| --- | --- |
| BSA | 1% (g/100 ml) |
| $ZnCl_2$ | 0.1 mM |
| NaCl | 175 g/L |
| $CaCl_2$ | 5 mM |
| $MgCl_2$ | 1 mM |
| Proclin 300 | 0.05% (g/100 ml) |
| Tris | 50 mM |
| pH was adjusted with HCl | to 7.5 |

As shown in Table 4, in the enzyme solution, the AP lost 1% of its activity after two weeks of the accelerated stability test. In this Example, the concentration of NaCl added is higher than that of Example 3, calcium ions have been added, and no casein or gelatin is present

TABLE 4

| | Residual AP activity | | | |
| --- | --- | --- | --- | --- |
| | Days of the test | | | |
| | Day 3 | Day 8 | Day 14 | Day 16 |
| Residual activity percent | 99% | 96% | 99% | 99% |

Example 5

An amount of AP was incorporated into the stabilizer solution formulated as below to form an enzyme solution as described in Example 1.

The stabilizer solution was formulated as follows:

| | |
| --- | --- |
| BSA | 1% (g/100 ml) |
| $ZnCl_2$ | 0.1 mM |
| NaCl | 175 g/L |
| Glycerol | 5% (g/100 ml) |
| Mannitol | 1% (g/100 ml) |
| $MgCl_2$ | 1 mM |
| Proclin 300 | 0.05% (g/100 ml) |
| Tris | 50 mM |
| pH was adjusted with HCl | to 7.5 |

As shown in Table 5, in the enzyme solution, the AP lost 2% of its activity after two weeks of the accelerated stability test. In this Example, no calcium ions were added, but glycerol and mannitol were present.

TABLE 5

| | Residual AP activity | | | |
| --- | --- | --- | --- | --- |
| | Days of the test | | | |
| | Day 3 | Day 8 | Day 14 | Day 16 |
| Residual activity percent | 99% | 99% | 98% | 92% |

Example 6

An amount of AP was incorporated into the stabilizer solution formulated as below to form an enzyme solution as described in Example 1.

The stabilizer solution was formulated as follows:

| | |
| --- | --- |
| BSA | 1% (g/100 ml) |
| $ZnCl_2$ | 0.1 mM |
| NaCl | 175 g/L |
| TritonX-100 | 0.5% |
| $MgCl_2$ | 1 mM |
| Proclin 300 | 0.05% (g/100 ml) |
| Tris | 50 mM |
| pH was adjusted with HCl | to 7.5 |

As shown in Table 6, in the enzyme solution, the AP lost 3% of its activity after two weeks of the accelerated stability test. In this Example, a surfactant was added, and no glycerol or mannitol is present.

TABLE 6

| Residual AP activity | | | | |
|---|---|---|---|---|
| | Days of the test | | | |
| | Day 3 | Day 8 | Day 14 | Day 16 |
| Residual activity percent | 99% | 99% | 97% | 97% |

Example 7

An amount of AP was incorporated into the stabilizer solution formulated as below to form an enzyme solution as described in Example 1.

The stabilizer solution was formulated as follows:

| | |
|---|---|
| BSA | 1% (g/100 ml) |
| $ZnCl_2$ | 0.1 mM |
| NaCl | 60 g/L |
| Sucrose | 5% (g/100 ml) |
| PEG20000 | 1% (g/100 ml) |
| $MgCl_2$ | 1 mM |
| Proclin 300 | 0.05% (g/100 ml) |
| Tris | 50 mM |
| pH was adjusted with HCl | to 7.5 |

As shown in Table 7, in the enzyme solution, the AP lost 2% of its activity after two weeks of accelerated stability test. In this Example, sucrose and PEG 20000 were present, but no surfactant.

TABLE 7

| Residual AP activity | | | | |
|---|---|---|---|---|
| | Days of the test | | | |
| | Day 3 | Day 8 | Day 14 | Day 16 |
| Ratio of residual activity | 98% | 98% | 98% | 94% |

Example 8

A stabilizer formulated as below was added to a solution of AP labeled thyroxine ($T_4$), a solution of AP labeled mouse anti-human Thyroid Stimulating Hormone (TSH), and a solution of AP labeled mouse anti-human chorinonic gonadotrophin (HCG), respectively, and the resulted enzymatic conjugate solution was subjected to an accelerated stability test in a thermostat at 37° C. and a constant humidity. The enzyme conjugate solution was then analyzed with a Mindray automatic biochemical analyzer BS300 and an accessory AP assay kit to determine the ratio of residual AP activity in the enzyme conjugate solution (as a percentage of the activity after the accelerated stability test to that before the accelerated stability test).

The stabilizer solution was formulated as follows:

| | |
|---|---|
| BSA | 1% (g/100 ml) |
| $ZnCl_2$ | 0.1 mM |
| NaCl | 30 g/L |
| Tween 80 | 0.5% |
| $MgCl_2$ | 1 mM |
| Proclin 300 | 0.05% (g/100 ml) |
| Tris | 50 mM |
| pH was adjusted with HCl | to 8.0 |

As shown in Table 8, in the enzyme conjugate solutions, the three conjugates of AP each lost less than 7% of their enzymatic activity after two weeks of the accelerated stability test. For the AP labeled mouse anti-human TSH, the loss of enzymatic activity was less than 8% after three weeks.

TABLE 8

| Residual alkaline phosphatase activity | | | | |
|---|---|---|---|---|
| | Days of accelerated stability test | | | |
| | Day 7 | Day 9 | Day 16 | Day 21 |
| Residual activity of the AP labeled thyroxine ($T_4$) | 95% | 95% | 93% | 82% |
| Residual activity of the AP labeled murine anti-human Thyroid Stimulating Hormone (TSH) | 94% | 93% | 94% | 92% |
| Residual activity of the AP labeled murine anti-human chorinonic gonadotrophin (HCG) | 92% | 94% | 94% | 88% |

As shown in the above Examples, the reagents disclosed herein sufficiently stabilize the enzymatic activity of AP or conjugates thereof for at least two weeks.

Although the present disclosure has been illustrated by way of the above Examples thereof, it will be appreciated by those skilled in the art that various changes, alterations and modifications may be made to the present disclosure without departing from the spirit and scope of the present disclosure as claimed.

The invention claimed is:

1. A method for stabilizing alkaline phosphatase or a conjugate thereof, the method comprising:
   mixing alkaline phosphatase or a conjugate thereof with an aqueous alkaline phosphatase stabilizer solution;
   wherein the aqueous alkaline phosphatase stabilizer solution comprises:
   a protein selected from at least one of the following: albumin, casein, and gelatin;
   magnesium and calcium ions, wherein the magnesium and calcium ions together have a concentration in the range of between about 0.001 and about 0.01 mol/L;
   zinc ions, wherein the zinc ions have a concentration in the range of between about 0.01 and about 0.2 mmol/L; and
   sodium ions, wherein the sodium ions have a concentration in the range of between about 0.5 and about 3.0 mol/L.

2. The method of claim 1, wherein the sodium ions in the aqueous alkaline phosphatase stabilizer solution are derived from sodium chloride.

3. The method of claim 2, wherein the aqueous alkaline phosphatase stabilizer solution contains from about 30 g/L to about 175 g/L of sodium chloride.

4. The method of claim 1, wherein the aqueous alkaline phosphatase stabilizer solution further comprises one or more protectant, wherein the one or more protectant is selected from at least one of the following: a polyol, a saccharide, a surfactant and a polyethylene glycol.

5. The method of claim 4, wherein the polyol is selected from at least one of the following: glycerol, mannitol, sorbitol, inositol and xylitol.

6. The method of claim 4, wherein the saccharide is selected from at least one of the following: galactose, lactose, fructose, sucrose, and trehalose.

7. The method of claim 4, wherein the surfactant is a nonionic surfactant.

8. The method of claim 7, wherein the nonionic surfactant is either a sorbitan polyoxyethylene ether fatty acid ester or an alkylphenol polyoxyethylene ether.

9. The method of claim 8, wherein the sorbitan polyoxyethylene ether fatty acid ester is either a sorbitan polyoxyethylene ether lauric acid ester or a sorbitan polyoxyethylene ether oleic acid ester.

10. The method of claim 8, wherein the alkylphenol polyoxyethylene ether is an octylphenol polyoxyethylene ether.

11. The method of claim 4, wherein the polyethylene glycol has a molecular weight ranging from about 6,000 to about 20,000.

12. The method of claim 11, wherein the polyethylene glycol has a molecular weight of about 20,000.

13. The method of claim 1, wherein the aqueous alkaline phosphatase stabilizer solution further comprises a buffering agent.

14. The method of claim 1, wherein the aqueous alkaline phosphatase stabilizer solution further comprises a protease inhibitor.

15. A process for preparing a reagent of alkaline phosphatase or a conjugate thereof, the process comprising:
    mixing or dissolving alkaline phosphatase or a conjugate thereof in an aqueous alkaline phosphatase stabilizer solution;
    wherein the aqueous alkaline phosphatase stabilizer solution comprises:
        a protein selected from at least one of the following: albumin, casein, and gelatin;
        magnesium and calcium ions, wherein the magnesium and calcium ions together have a concentration in the range of between about 0.001 and about 0.01 mol/L;
        zinc ions, wherein the zinc ions have a concentration in the range of between about 0.01 and about 0.2 mmol/L;
        sodium ions, wherein the sodium ions have a concentration in the range of between about 0.5 and about 3.0 mol/L; and
        a nonionic surfactant, wherein the nonionic surfactant is an octylphenol polyoxyethylene ether type surfactant that is present in a concentration in the range of between about 0.1% and about 10% (w/v); and
    optionally drying the solution into a powder.

16. A process for preparing a reagent of alkaline phosphatase or a conjugate thereof, the process comprising:
    drying an aqueous alkaline phosphatase stabilizer solution to a powder;
    drying an aqueous solution of alkaline phosphatase or a conjugate thereof to a powder; and
    mixing the powders together;
    wherein the aqueous alkaline phosphatase stabilizer solution comprises:
        a protein selected from at least one of the following: albumin, casein and gelatin;
        magnesium and calcium ions, wherein the magnesium and calcium ions together have a concentration in the range of between about 0.001 and about 0.01 mol/L;
        zinc ions, wherein the zinc ions have a concentration in the range of between about 0.01 and about 0.2 mmol/L;
        sodium ions, wherein the sodium ions have a concentration in the range of between about 0.5 and about 3.0 mol/L; and
        a combination of glycerol and mannitol, wherein the combined concentration of glycerol and mannitol is between about 5% and about 10% (w/v).

* * * * *